United States Patent
Ahmed et al.

(10) Patent No.: US 11,395,633 B2
(45) Date of Patent: Jul. 26, 2022

(54) SYSTEMS AND METHODS FOR DETERMINING ENGAGEMENT OF A PORTABLE DEVICE

(71) Applicant: InvenSense, Inc., San Jose, CA (US)

(72) Inventors: Jibran Ahmed, Calgary (CA); Karthik Katingari, Milpitas, CA (US)

(*) Notice: Subject to any disclaimer, the term of this patent is extended or adjusted under 35 U.S.C. 154(b) by 304 days.

(21) Appl. No.: 16/589,017

(22) Filed: Sep. 30, 2019

(65) Prior Publication Data

US 2020/0029912 A1 Jan. 30, 2020

Related U.S. Application Data

(63) Continuation of application No. 15/220,874, filed on Jul. 27, 2016, now Pat. No. 10,426,407.

(51) Int. Cl.
*A61B 5/00* (2006.01)
*A61B 5/024* (2006.01)

(52) U.S. Cl.
CPC ............ *A61B 5/7221* (2013.01); *A61B 5/002* (2013.01); *A61B 5/02427* (2013.01); *A61B 5/6802* (2013.01); *A61B 5/6843* (2013.01); *A61B 5/6826* (2013.01); *A61B 2562/0219* (2013.01)

(58) Field of Classification Search
CPC ... A61B 5/7221; A61B 5/002; A61B 5/02427; A61B 5/6802; A61B 5/6843; A61B 5/6826; A61B 2562/0219
See application file for complete search history.

(56) References Cited

U.S. PATENT DOCUMENTS

2005/0177051 A1* 8/2005 Almen ............... A61B 5/02405
600/509
2013/0338478 A1* 12/2013 Hirota .................. A61B 5/0095
600/407

\* cited by examiner

*Primary Examiner* — Lindsey G Wehrheim (57) ABSTRACT

A portable device is provided having a motion sensor and an engagement sensor. A determination may be made whether the portable device is engaged with the platform. The data being output by the sensor may be used accordingly.

20 Claims, 5 Drawing Sheets

SYSTEMS AND METHODS FOR DETERMINING ENGAGEMENT OF A PORTABLE DEVICE

FIELD OF THE PRESENT DISCLOSURE

This disclosure generally relates to assessing characteristics of the association between a platform and a portable device, and more specifically to determining whether a wearable device is engaged with a user and interpreting data collected from a health monitoring sensor of the wearable device based at least in part on the determined engagement.

BACKGROUND

Developments in sensor technology, such as the use of microelectromechanical systems (MEMS), have enabled the incorporation of a wide variety of sensors into mobile devices. Non-limiting examples of such sensors include an accelerometer, a gyroscope, a magnetometer, a pressure sensor, a microphone, a proximity sensor, an ambient light sensor, an infrared sensor, and the like. One or more of these sensors, or others, may be used for a similarly wide variety of purposes, including monitoring, characterizing or analyzing quantities related to the health of a user. As an illustrative example only and without limitation, a health sensor may be a photoplethysmograph used to determine the pulse rate and/or blood oxygen saturation of a user by sensing changes in the amount of light absorbed by tissue. Accordingly, the quality of the data provided by the photoplethysmograph may depend on how securely the sensor is engaged with the user, otherwise movement of the sensor with respect to the user may produce erroneous signal components, such as may be attributed to varying amounts of ambient light being recorded. It should be appreciated that many other types of sensors may also be influenced by how a portable device incorporating them are associated with a platform, such as a user.

In light of these observations, it would be desirable to assess one or more characteristics of the association between a user and a portable device. For example, it would be desirable to determine whether a wearable device is engaged with a user, allowing the data being output by the sensor to be interpreted more accurately. Further, it would be desirable to validate data output by a sensor when it is determined the wearable device is engaged with the user. Still further, it would be desirable to utilize different algorithms or otherwise adjust the analysis of sensor data depending on whether the wearable device is engaged with the user or not. More generally, it would be desirable to use the determination of the engagement of any portable device with a platform when using sensor data, such as for aiding a navigational solution that uses motion sensor data provided by the portable device. The techniques of this disclosure satisfy these and other needs as described in the following materials. While the following discussion is in the context of MEMS sensors as used in portable devices, one of skill in the art will recognize that these techniques may be employed to any suitable sensor application as desired.

SUMMARY

This disclosure is directed to a method for determining engagement of a portable device with a platform. The method may involve obtaining motion sensor data for the portable device, obtaining engagement sensor data for the portable device and determining the portable device is exhibiting motion with respect to the platform when the engagement sensor data exceeds an engagement threshold, wherein the engagement threshold is based at least in part on the motion sensor data.

This disclosure also includes a portable device having a motion sensor, an engagement sensor and an engagement module configured to compare data from the engagement sensor to an engagement threshold, wherein the engagement threshold is based at least in part on data output by the motion sensor, and to determine the portable device is exhibiting motion with respect to a platform when the engagement sensor data exceeds an engagement threshold.

Still further, this disclosure includes a system for determining engagement of a portable device with a platform. The system may include a portable device having a motion sensor and an engagement sensor and an auxiliary device having an engagement module. The auxiliary device may receive data from the motion sensor and the engagement sensor such that the engagement module may compare data from the engagement sensor to an engagement threshold, wherein the engagement threshold is based at least in part on data output by the motion sensor, and may determine the portable device is exhibiting motion with respect to a platform when the engagement sensor data exceeds an engagement threshold.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings or chip embodiments. These and similar directional terms should not be construed to limit the scope of the disclosure in any manner.

In this specification and in the claims, it will be understood that when an element is referred to as being "connected to" or "coupled to" another element, it can be directly connected or coupled to the other element or intervening elements may be present. In contrast, when an element is referred to as being "directly connected to" or "directly coupled to" another element, there are no intervening elements present.

Some portions of the detailed descriptions which follow are presented in terms of procedures, logic blocks, processing and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "accessing," "receiving," "sending," "using," "selecting," "determining," "normalizing," "multiplying," "averaging," "monitoring," "comparing," "applying," "updating," "measuring," "deriving" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the exemplary wireless communications devices may include components other than those shown, including well-known components such as a processor, memory and the like.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Of course, many modifications may be made to this configuration without departing from the scope or spirit of the claimed subject matter.

The various illustrative logical blocks, modules, circuits and instructions described in connection with the embodiments disclosed herein may be executed by one or more processors, such as one or more digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structure or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Unless defined otherwise, all technical and scientific terms used herein have the same meaning as commonly understood by one having ordinary skill in the art to which the disclosure pertains.

Finally, as used in this specification and the appended claims, the singular forms "a," "an" and "the" include plural referents unless the content clearly dictates otherwise.

As noted above, the techniques of this disclosure may be used to determine whether a portable device is engaged with a platform and using data being output by the sensor accordingly. For example, data output by a sensor may be validated when it is determined a wearable device is engaged with a user. Alternatively or in addition, different algorithms may be employed or other processing techniques may be applied depending on whether the wearable device is engaged with the user or not. More generally, a determination of the engagement of a portable device with a platform may be used for other purposes, such as for aiding a navigational solution that uses motion sensor data provided by the portable sensor.

Figure 1:
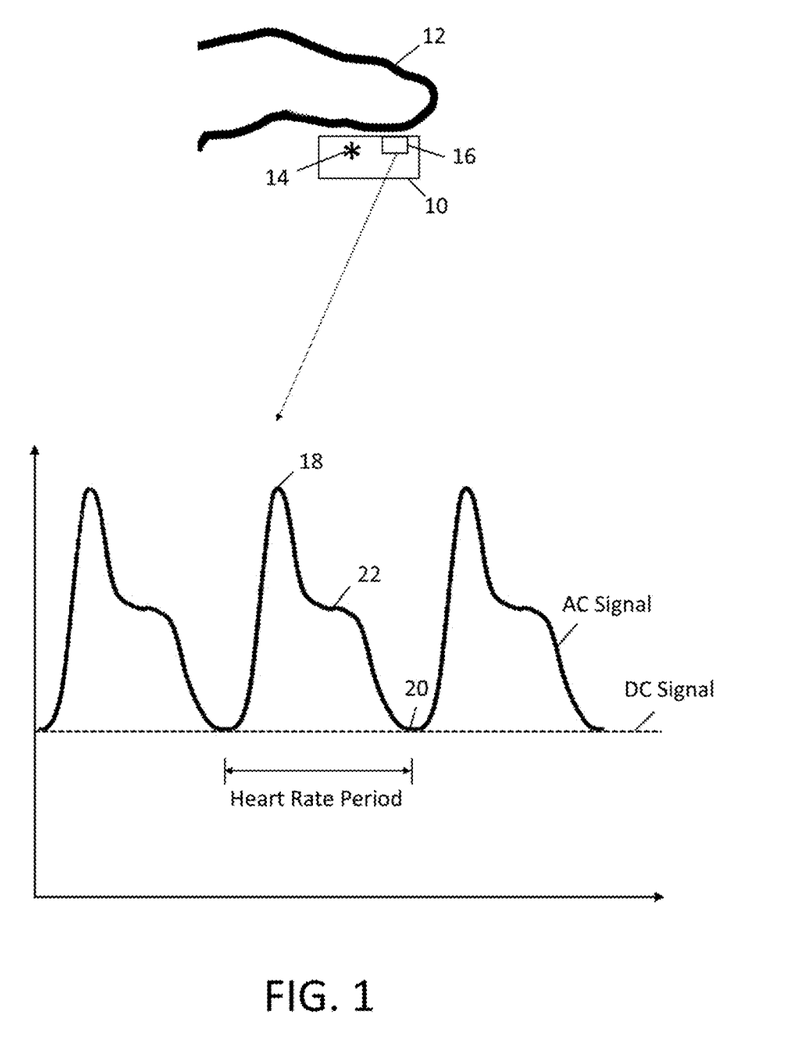
FIG. 1 is a schematic diagram of a photoplethysmograph in accordance with an embodiment.

To help illustrate aspects of this disclosure, FIG. 1 schematically depicts a photoplethysmograph and the corresponding data output. In this embodiment, photoplethysmograph 10 is configured as a portable, wearable device that may be worn on a user's finger 12 as shown. Other designs may be adapted as warranted depending on where the photoplethysmograph is to be worn, such as an ear lobe, a wrist or any other suitable location. Although a photoplethysmograph is the health sensor described in this embodiment, any other health or biophysical sensor such as electrocardiogram patches or other electrical sensors, blood pressure monitors, or ultrasound monitors for example are within the context of the disclosure. Further, these techniques may also be applied to any type of sensor that may incorporated into a portable device if the sensor is influenced by the association between the portable device and its conveying platform. As an illustrative example only, a portable device may have one or more motion sensors which may output data that is interpreted in light of an assessment of the engagement between the portable device and a platform, which may be a user, a vehicle or other moving element. Correspondingly, a navigation solution derived for the portable device may be aided by considering the engagement with the platform, as the motion sensor data may correspond more directly with motion of the platform when the portable device is engaged with the platform.

The components of photoplethysmograph 10 used to monitor aspects of a user's cardiovascular system include a light source 14, typically infrared and/or red, and a light sensor 16. In one embodiment, light source 14 may be a green light emitting diode (LED). Light emitted by light source 14 transmitted through and/or reflected by the tissue in the user's finger 12 may be absorbed to varying degrees. Skin, bone and other tissue, as well as venous blood, represents a substantially constant absorption that is unrelated to the user's heart rate. As such, a direct current (DC) signal component is present in the output of light sensor 16 as indicated. In contrast, the arterial blood volume changes in coordination with the user's heart rate, resulting in an alternating current (AC) signal component. The characteristics of the AC signal correspond to features of the heart rate, such by exhibiting maxima and minima at the systolic point 18 and the diastolic point 20, respectively, with an intermediate dicrotic notch 22. The period between sequential features may be calculated to provide an accurate measure of the user's heart rate.

As will be appreciated, when photoplethysmograph 10 is engaged with finger 12, the ambient light received by light sensor 16 will remain more constant. Further, engagement of photoplethysmograph 10 with finger 12 will also maintain the relationship of light source 14 and light sensor 16 with the tissue of finger 12, so that the path traveled by the light as it reflects through and/or is transmitted by the tissue also remains more constant. In turn, these characteristics help stabilize the DC component of the signal received by light sensor 16 so that the variable AC component more accurately reflects the changes in arterial blood due to the user's heart rate. Conversely, when photoplethysmograph 10 is not engaged with finger 12, the amount of ambient light to which light sensor 16 is exposed may vary, degrading the quality of the AC signal component. Similarly, changes in the relationship between light source 14 and light sensor 16 with the tissue of finger 12 may also change the amount of light absorbed by non-pulsatile components, also degrading signal quality.

Accordingly, the techniques of this disclosure may include providing photoplethysmograph 10 with an engagement sensor in order to determine characteristics of the association with the user. One exemplary embodiment is depicted with high level schematic blocks in FIG. 2. As will be appreciated, photoplethysmograph 10 may be implemented as a device or apparatus, such as a wearable device designed to position light source 14 and light sensor 16 at a desired location of the user, such as a fingertip, an ear lobe, a wrist or any other suitable location. In other embodiments, any portable device that can be moved in space by a user and its motion, location and/or orientation in space therefore sensed may be employed. For example, such a portable device may be a mobile phone (e.g., smartphone, cellular phone, a phone running on a local network, or any other telephone handset), tablet, personal digital assistant (PDA), video game player, video game controller, navigation device, wearable device (e.g., glasses, watch, belt clip, ring, garment, shoe), fitness tracker, virtual or augmented reality equipment, mobile internet device (MID), personal navigation device (PND), digital still camera, digital video camera, binoculars, telephoto lens, portable music, video or media player, remote control, or other handheld device, or a combination of one or more of these devices. Similarly, the portable device may have any combination of health sensors or other types of sensors that may benefit from the determination of whether the portable device is engaged with a platform.

Figure 2:
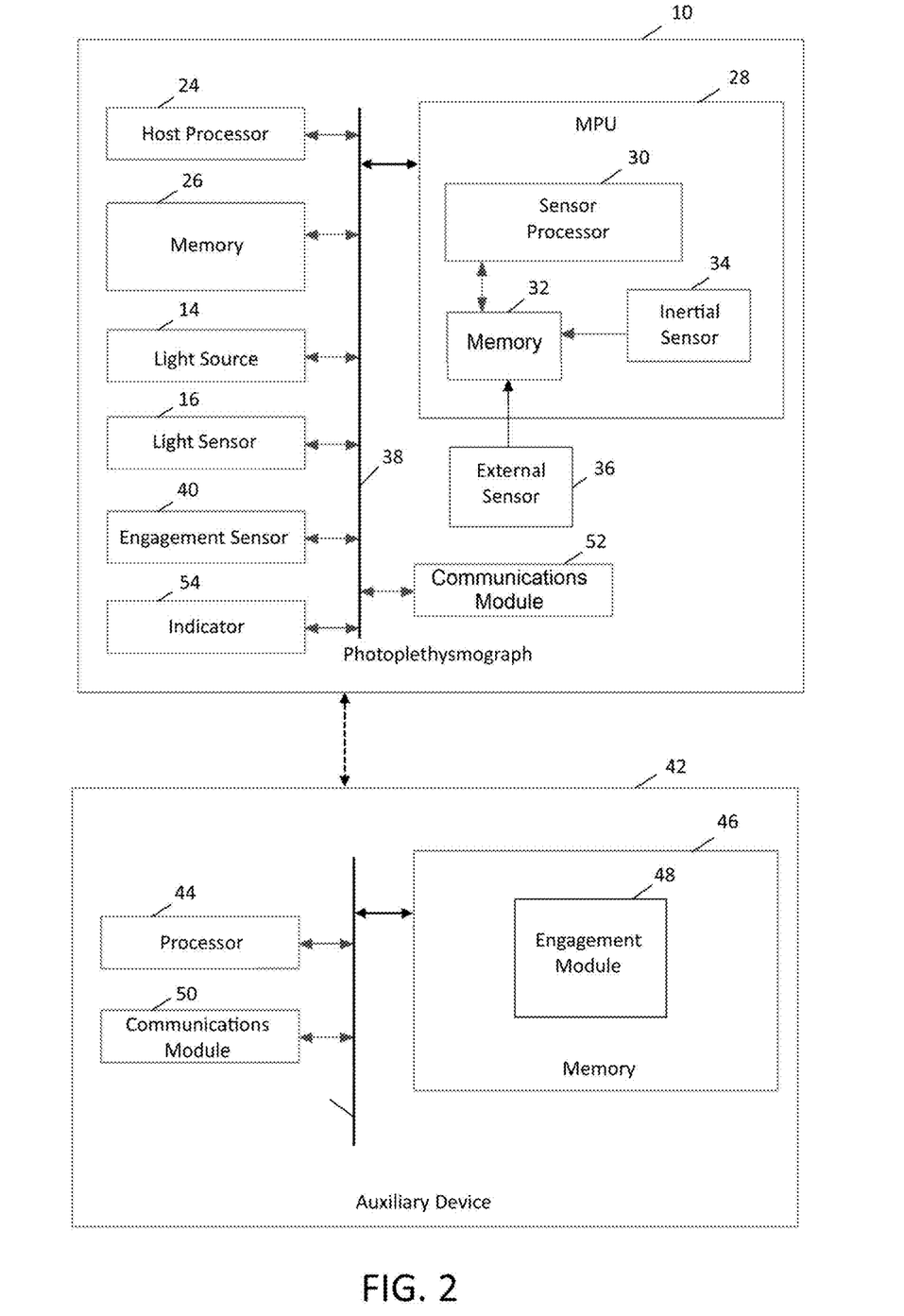
FIG. 2 is a high level schematic diagram of a portable device configured as a photoplethysmograph in accordance with an embodiment.

As shown, photoplethysmograph 10 includes a host processor 24, which may be one or more microprocessors, central processing units (CPUs), or other processors to run software programs, which may be stored in memory 26, associated with the functions of photoplethysmograph 10. Multiple layers of software can be provided in memory 26, which may be any combination of computer readable medium such as electronic memory or other storage medium such as hard disk, optical disk, etc., for use with the host processor 24. For example, an operating system layer can be provided for photoplethysmograph 10 to control and manage system resources in real time, enable functions of application software and other layers, and interface application programs with other software and functions of photoplethysmograph 10. Similarly, different software application programs such as menu navigation software, games, camera function control, navigation software, communications software, such as telephony or wireless local area network (WLAN) software, or any of a wide variety of other software and functional interfaces can be provided. In some embodiments, multiple different applications can be provided on a single photoplethysmograph 10, and in some of those embodiments, multiple applications can run simultaneously.

Photoplethysmograph 10 includes at least one sensor assembly, as shown here in the form of integrated motion processing unit (MPU™) 28 featuring sensor processor 30, memory 32 and inertial sensor 34. Memory 32 may store algorithms, routines or other instructions for processing data output by inertial sensor 34 and/or other sensors as described below using logic or controllers of sensor processor 30, as well as storing raw data and/or motion data output by inertial sensor 34 or other sensors. Inertial sensor 34 may be one or more sensors for measuring motion of photoplethysmograph 10 in space. Depending on the configuration, MPU 28 measures one or more axes of rotation and/or one or more axes of acceleration of the device. In one embodiment, inertial sensor 34 may include rotational motion sensors or linear motion sensors. For example, the rotational motion sensors may be gyroscopes to measure angular velocity along one or more orthogonal axes and the linear motion sensors may be accelerometers to measure linear acceleration along one or more orthogonal axes. In one aspect, three gyroscopes and three accelerometers may be employed, such that a sensor fusion operation performed by sensor processor 30, or other processing resources of photoplethysmograph 10, combines data from inertial sensor 34 to provide a six axis determination of motion. As desired, inertial sensor 34 may be implemented using Micro Electro Mechanical System (MEMS) to be integrated with MPU 28 in a single package. Exemplary details regarding suitable configurations of host processor 24 and MPU 28 may be found in co-pending, commonly owned U.S. patent application Ser. No. 11/774,488, filed Jul. 6, 2007, and Ser. No. 12/106,921, filed Apr. 11, 2008, which are hereby incorporated by reference in their entirety. Suitable implementations for MPU 28 in photoplethysmograph 10 are available from InvenSense, Inc. of Sunnyvale, Calif.

Alternatively or in addition, photoplethysmograph 10 may implement a sensor assembly in the form of external sensor 36. This is optional and not required in all embodiments. External sensor 36 may represent one or more sensors as described above, such as an accelerometer and/or a gyroscope, or any other suitable sensor configured to measure one or more aspects about the environment surrounding device 16. This is optional and not required in all embodiments. As used herein, "external" means a sensor that is not integrated with MPU 28 and may be remote or local to photoplethysmograph 10. For example, a barometer and/or a magnetometer may be used to refine position determinations made using inertial sensor 34. In one embodiment, external sensor 36 may include a magnetometer measuring along three orthogonal axes and output data to be fused with the gyroscope and accelerometer inertial sensor data to provide a nine axis determination of motion. In another embodiment, external sensor 36 may also include a barometer to provide an altitude determination that may be fused with the other sensor data to provide a ten axis determination of motion. Although described in the context of one or more sensors being MEMS based, the techniques of this disclosure may be applied to any sensor design or implementation.

In the embodiment shown, host processor 24, memory 26, MPU 28 and other components of photoplethysmograph 10 may be coupled through bus 38, which may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, a serial peripheral interface (SPI) or other equivalent. Depending on the architecture, different bus configurations may be employed as desired. For example, additional buses may be used to couple the various components of photoplethysmograph 10, such as by using a dedicated bus between host processor 24 and memory 26.

As noted above, photoplethysmograph 10 also includes an engagement sensor 40. Depending on the implementation, engagement sensor 40 may be a proximity sensor, a distance sensor or any other sensor that outputs a signal corresponding to the range between photoplethysmograph 10 and an adjacent object. Engagement sensor 40 may detect changes in an electromagnetic field to determine whether an object is adjacent the sensor. In other embodiments, other quantities may be measured to determine the relative distance to an object, including sound waves using an ultrasonic transducer, for example. Engagement sensor 40 may be coupled to bus 38, may be coupled to MPU 28 as with external sensor 36, or may be implemented using any other suitable architecture. Further, in some embodiments, light source 14 and light sensor 16 may be used to provide the functionality of an engagement sensor. As discussed above, a lack of engagement between photoplethysmograph 10 and finger 12 may result in variation in the DC signal component. Photoplethysmograph 10 may be configured with a feedback loop to provide a desired stable DC signal component by altering the current used to drive light source 14. Correspondingly, the drive current may be sampled, such as with an analog to digital converter (ADC) to provide a signal that represents engagement between photoplethysmograph 10 and finger 12. For example, a relatively more constant drive current may indicate engagement while a relatively more variable drive current may indicate a lack of engagement. Reference values may be established as warranted during calibration of photoplethysmograph 10.

In this exemplary system, photoplethysmograph 10 communicates raw sensor data at least with regard to inertial sensor 34 and engagement sensor 40 to auxiliary device 42, which may include processor 44 that is in communication with memory 46 over bus 48. Auxiliary device 42 may operate in conjunction with photoplethysmograph 10, such as by providing a more convenient user interface and/or increased processing resources. As an illustration, auxiliary device 42 may be a smartphone. Processor 44 may execute instructions stored in memory 46 that are represented as functional blocks, including engagement module 48, which may perform the operations described in this disclosure to characterize the association between a portable device, such as photoplethysmograph 10, and a platform, such as a user. Auxiliary device 42 may also include a communications module 50 to receive raw sensor data sent by communications module 52 of photoplethysmograph 10. The communications modules may employ any suitable protocol, including a shorter range, low power communication protocol such as BLUETOOTH®, ZigBee®, ANT or a longer range communication protocol, such as a transmission control protocol, internet protocol (TCP/IP) packet-based communication, accessed using a wireless local area network (WLAN), cell phone protocol or the like. In other embodiments, a wired connection may be employed. In general, the system depicted in FIG. 2 may embody aspects of a networked or distributed computing environment. Photoplethysmograph 10 and auxiliary device 42 may communicate either directly or indirectly, such as through multiple interconnected networks. As will be appreciated, a variety of systems, components, and network configurations, topologies and infrastructures, such as client/server, peer-to-peer, or hybrid architectures, may be employed to support distributed computing environments.

Multiple layers of software may be employed as desired and stored in any combination of memory 26, memory 32, memory 46, or other suitable location. For example, a motion algorithm layer can provide motion algorithms that provide lower-level processing for raw sensor data provided from the motion sensors and other sensors. A sensor device driver layer may provide a software interface to the hardware sensors of photoplethysmograph 10. Further, a suitable application program interface (API) may be provided to facilitate communication between host processor 24 and MPU 28, for example, to transmit desired sensor processing tasks. Similarly, any suitable division of processing resources may be employed whether within photoplethysmograph 10, auxiliary device 42, or among any plurality of other devices. For example, processor 44 may receive sensor data from light sensor 16 using communication module 50 and execute instructions from engagement module 48 to determine engagement between photoplethysmograph 10 and the user. In turn, the engagement information may be communicated to photoplethysmograph 10 for use in processing data, such as by processor 24. Alternatively, processor 44 may also receive output from light sensor 16 and process the data locally. Further, aspects implemented in software may include but are not limited to, application software, firmware, resident software, microcode, etc., and may take the form of a computer program product accessible from a non-transitory computer-usable or computer-readable medium providing program code for use by or in connection with a computer or any instruction execution system, such as host processor 24, sensor processor 30, processor 44, a dedicated processor or any other processing resources of photoplethysmograph 10, auxiliary device 42 or other remote processing resources, or may be implemented using any desired combination of software, hardware and firmware. Further, any or all of the functions may be performed by photoplethysmograph 10 itself, such as by implementing engagement module 48 in memory 26 or any other suitable system architecture.

Correspondingly, engagement of a portable device, such as photoplethysmograph 10, with a platform, such as a user, may include sampling data from inertial sensor 34 and engagement sensor 40 and determining the portable device is exhibiting motion with respect to the platform when the motion sensor data exceeds a motion threshold when the engagement sensor data exceeds an engagement threshold. In some embodiments, photoplethysmograph 10 may include indicator 54 to communicate to a user the determination provided by engagement module 48, allowing the user to adjust the positioning or connection of photoplethysmograph 10. Any suitable indication may be used, including visual, auditory or tactile. For example, photoplethysmograph 10 may have a display provided as part of the user interface which may function as indicator 54. Alternatively, a dedicated light or the like may be used to signal engagement. In other embodiments, an indicator may be provided on auxiliary device 42 in a similar manner.

Figure 3:
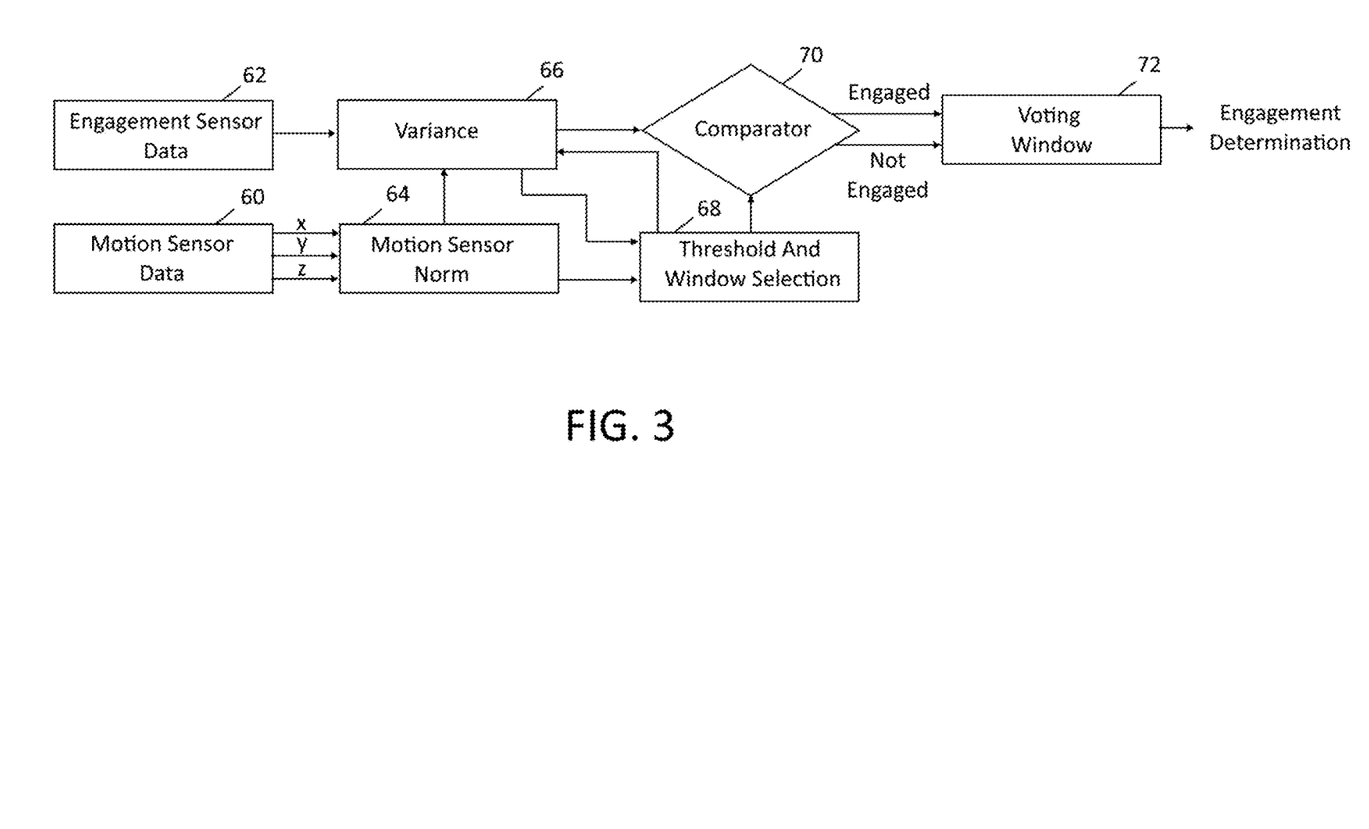
FIG. 3 depicts a routine representing the operations of an engagement module in accordance with an embodiment.

A representative routine of the operations performed by engagement module 48 is depicted in FIG. 3. Beginning with 60, motion sensor data may be obtained for a plurality of epochs over a given time period, such as from inertial sensor 34 and/or external sensor 36, for photoplethysmograph 10. In this embodiment, sensor data is provided for three orthogonal axes, x, y and z, although fewer axes may be employed or may be combined, and may be obtained from a gyroscope, an accelerometer, or another suitable motion sensor. In 62, engagement sensor data is obtained, such as from engagement sensor 40 or from the operation of light source 14 and light sensor 16 as described above. The intensity of motion experienced by photoplethysmograph 10 is determined by computing a norm of the motion sensor data, such as the Euclidian, distance or 2-norm, in 64. The variance of the engagement sensor data is determined in 66, and may be assessed over an adaptive window of samples. The size of the window may be adjusted in 68 based on the norm of the motion sensor data, typically by correlating the size of the window with the intensity of motion as determined from the norm. Based at least in part on motion intensity and engagement sensor variance, a suitable engagement threshold may also be set in 68. Correspondingly, the variance of the engagement sensor data is compared to the engagement threshold in 70, with a engaged or not engaged determination returned for the current epoch. In 72, a voting window may be employed to help reduce the risk of a false positive by accumulating results over a series of epochs. The output of 72 may indicate whether engaged or not engaged depending on the majority (or a more stringent test if desired) of determinations over the voting window. In some embodiments, it may be desirable to return a result of no determination if the voting is inconclusive.

As an example only and without limitation, motion sensor data may be sampled at 25 Hz and the norm calculated for the preceding 32 samples. Engagement sensor 40 may be polled at the same rate with an initial window of 64 samples, that may be adjusted up or down depending on the norm of the motion sensor data. A voting window of five epochs may be employed. In some embodiments, it may be desirable to conserve power by not sampling engagement sensor 40 until the sensed motion exceeds a suitable threshold.

Figure 4:
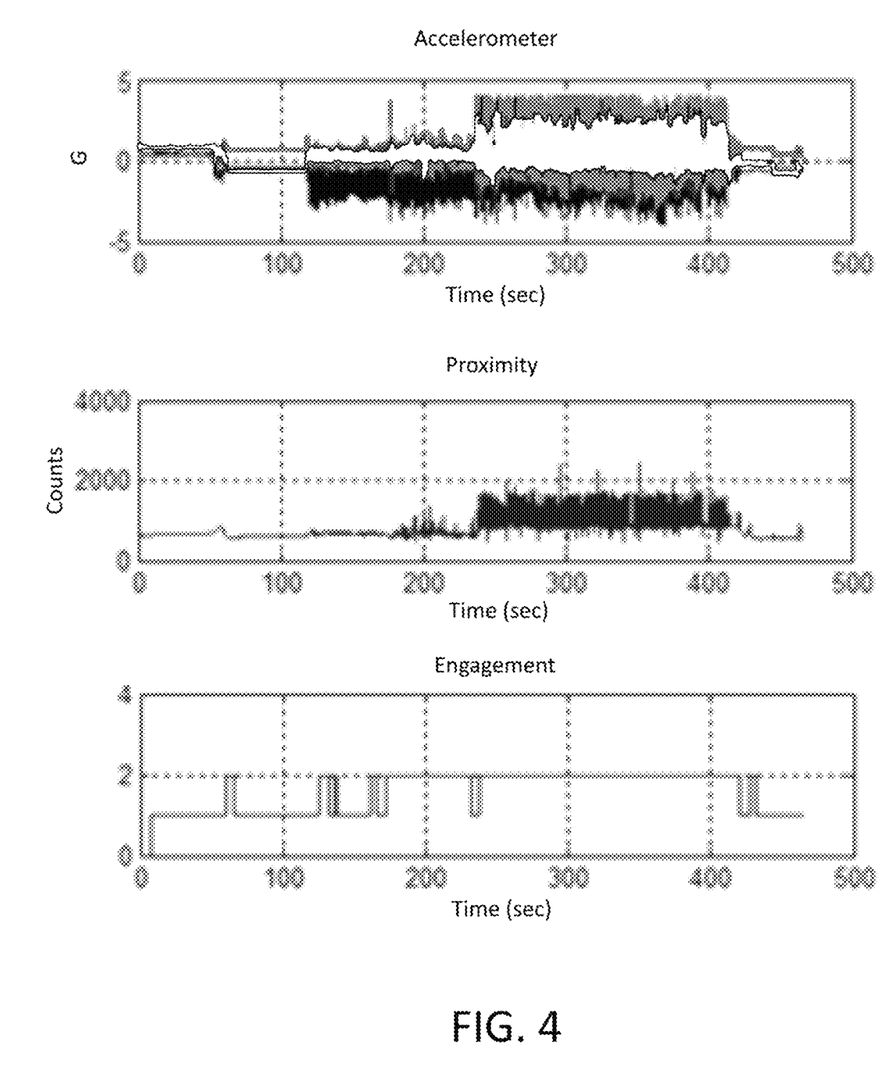
FIG. 4 depicts test data showing accelerometer data and proximity data used in making a determination of not engaged in accordance with an embodiment.
Figure 5:
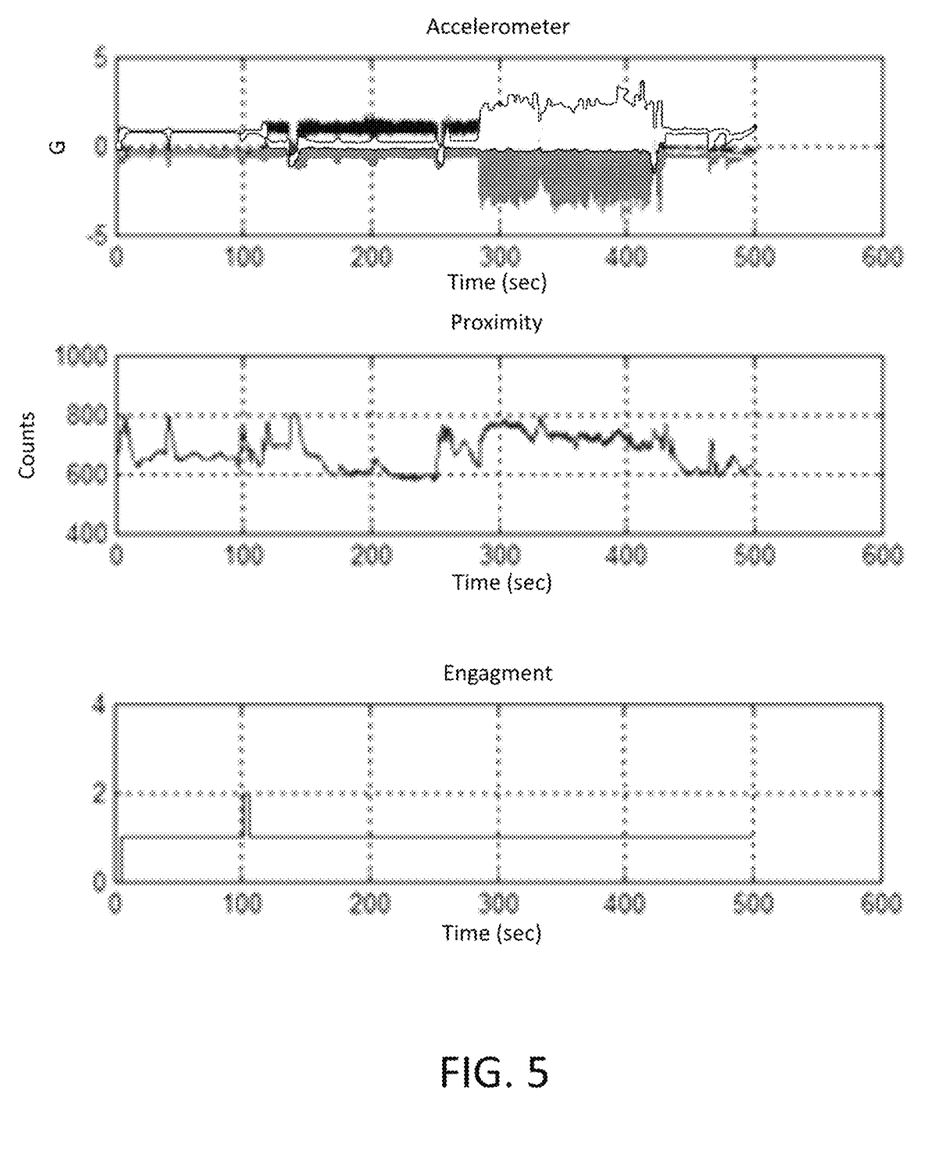
FIG. 5 depicts test data showing accelerometer data and proximity data used in making a determination of engaged in accordance with an embodiment.

To help illustrate application of these techniques, tests were conducted and the results are depicted in FIGS. 4 and 5. In each figure, the top graph shows the output of inertial sensor 34, which is an accelerometer in this embodiment. The middle graph shows the output of the engagement sensor 40, a proximity sensor in this embodiment. The bottom graph shows the output of voting window 72, with an engaged determination represented by 1 and a not engaged determination represented by 2. From these results, it may be possible to make a not engaged determination with approximately 90% confidence and an engaged determination with approximately 95% confidence.

In one aspect, the motion sensor data may be accelerometer data.

In one aspect, the motion sensor data may be gyroscope data.

In one aspect, the engagement sensor is selected from the group consisting of a proximity sensor and a distance sensor.

In one aspect, the engagement sensor may be a light sensor.

In one aspect, the engagement threshold may be based at least in part on a norm of the motion sensor data over a window of sequential samples. The engagement threshold may be positively correlated with the norm of the motion sensor data. The method may also involve adjusting a size of the window of sequential samples. The size of the window of sequential samples may be positively correlated with an amount of motion indicated by the motion sensor data.

In one aspect, the portable device may be a health sensor and wherein the platform is a user. The health sensor may be a photoplethysmograph sensor, further comprising determining validity for photoplethysmograph sensor data based at least in part on whether the portable device is exhibiting motion with respect to the user. The method may also involve employing an algorithm to evaluate photoplethysmograph sensor data that is based at least in part on whether the portable device is exhibiting motion with respect to the user. An indication may be provided to the user whether the engagement sensor data exceeds an engagement threshold In one aspect, the method may involve employing an algorithm to provide a navigation solution for the portable device that is based at least in part on whether the portable device is exhibiting motion with respect to the user.

In the described embodiments, an electronic device incorporating a sensor may employ a motion tracking module also referred to as Motion Processing Unit (MPU) that includes at least one sensor in addition to electronic circuits. The sensor, such as a gyroscope, a compass, a magnetometer, an accelerometer, a microphone, a pressure sensor, a proximity sensor, or an ambient light sensor, among others known in the art, are contemplated. Some embodiments include accelerometer, gyroscope, and magnetometer, which each provide a measurement along three axes that are orthogonal relative to each other referred to as a 9-axis device. Other embodiments may not include all the sensors or may provide measurements along one or more axes. The sensors may be formed on a first substrate. Other embodiments may include solid-state sensors or any other type of sensors. The electronic circuits in the MPU receive measurement outputs from the one or more sensors. In some embodiments, the electronic circuits process the sensor data. The electronic circuits may be implemented on a second silicon substrate. The first substrate may be vertically stacked, attached and electrically connected to the second substrate in a single semiconductor chip.

In one embodiment, the first substrate is attached to the second substrate through wafer bonding, as described in commonly owned U.S. Pat. No. 7,104,129, which is incorporated herein by reference in its entirety, to simultaneously provide electrical connections and hermetically seal the MEMS devices. This fabrication technique advantageously enables technology that allows for the design and manufacture of high performance, multi-axis, inertial sensors in a very small and economical package. Integration at the wafer-level minimizes parasitic capacitances, allowing for improved signal-to-noise relative to a discrete solution. Such integration at the wafer-level also enables the incorporation of a rich feature set which minimizes the need for external amplification.

In the described embodiments, raw data refers to measurement outputs from the sensors which are not yet processed. Motion data refers to processed raw data. Processing may include applying a sensor fusion algorithm or applying any other algorithm. In the case of the sensor fusion algorithm, data from one or more sensors are combined to provide an orientation of the device. In the described embodiments, a MPU may include processors, memory, control logic and sensors among structures.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the present invention.

What is claimed is:

1. A portable health monitor, comprising:
   an ultrasonic sensor configured to output ultrasonic sensor data for a user;
   a health monitor module configured to determine a health characteristic of the user based at least in part on the ultrasonic sensor data; and
   an engagement module configured to:
   a) evaluate relative motion between the health monitor and the user based at least in part on comparing engagement data derived from the ultrasonic sensor with an engagement threshold;
   b) validate the determined health characteristic based at least in part on the relative motion evaluation; and
   c) provide an indication to the user when the engagement data exceeds the engagement threshold.

2. The portable health monitor of claim 1, wherein the determined health characteristic is related to the user's heart rate.

3. The portable health monitor of claim 1, wherein the determined health characteristic is related to the user's blood pressure.

4. The portable health monitor of claim 1, wherein the determined health characteristic is related to the user's cardiovascular system.

5. The portable health monitor of claim 1, wherein the engagement threshold is based at least in part on a measure of distance derived using the ultrasonic sensor data.

6. The portable health monitor of claim 1, further comprising a motion sensor configured to output motion sensor data, wherein the evaluation of relative motion is further based at least in part on the motion sensor data.

7. The portable health monitor of claim 6, wherein the engagement threshold is based at least in part on the motion sensor data.

8. The portable health monitor of claim 1, further comprising a supplemental engagement sensor selected from the group consisting of a proximity sensor and a distance sensor, wherein the engagement module is further configured to evaluate relative motion between the health monitor and the user based at least in part on data output by the supplemental engagement sensor.

9. The portable health monitor of claim 1, further comprising a supplemental engagement sensor comprising a light sensor, wherein the engagement module is further configured to evaluate relative motion between the health monitor and the user based at least in part on data output by the supplemental engagement sensor.

10. The portable health monitor of claim 1, wherein the evaluation of relative movement is based at least in part on variance of the engagement data.

11. The portable health monitor of claim 1, wherein the determination of the health characteristic is adjusted based at least in part on the evaluation of relative motion.

12. The portable health monitor of claim 1, wherein the evaluation of relative movement is with respect to the user's finger.

13. A method for determining engagement of a portable health monitor with a user, comprising:
   obtaining ultrasonic sensor data for the portable health monitor;
   determining a health characteristic of the user based at least in part on the ultrasonic sensor data;
   evaluating relative motion between the health monitor and the user based at least in part on comparing engagement data derived from the ultrasonic sensor data with an engagement threshold;
   validating the determined health characteristic based at least in part on the relative motion evaluation; and providing an indication to the user whether the engagement data exceeds the engagement threshold.

14. The method of claim 13, wherein the determined health characteristic is related to the user's cardiovascular system.

15. The method of claim 13, further comprising obtaining motion sensor data for the portable health monitor, wherein the evaluation of relative motion is based at least in part on the motion sensor data.

16. The method of claim 13, wherein the engagement threshold is based at least in part on a measure of distance derived using the ultrasonic sensor data.

17. The method of claim 13, wherein the evaluation of relative movement is based at least in part on variance of the engagement data.

18. The method of claim 13, wherein the determination of the health characteristic is adjusted based at least in part on the evaluation of relative motion.

19. A portable health monitor, comprising:
- an ultrasonic sensor configured to output ultrasonic sensor data for a user;
- a health monitor module configured to determine a health characteristic of the user based at least in part on the ultrasonic sensor data; and
- an engagement module configured to:
  a) evaluate relative motion between the health monitor and the user based at least in part on comparing engagement data derived from the ultrasonic sensor with an engagement threshold; and
  b) validate the determined health characteristic based at least in part on the relative motion evaluation;

wherein the determined health characteristic is related to the user's blood pressure.

20. A portable health monitor, comprising:
- an ultrasonic sensor configured to output ultrasonic sensor data for a user;
- a health monitor module configured to determine a health characteristic of the user based at least in part on the ultrasonic sensor data; and
- an engagement module configured to:
  a) evaluate relative motion between the health monitor and the user based at least in part on comparing engagement data derived from the ultrasonic sensor with an engagement threshold; and
  b) validate the determined health characteristic based at least in part on the relative motion evaluation;

wherein the portable health monitor further comprises a supplemental engagement sensor selected from the group consisting of a light sensor, a proximity sensor and a distance sensor, wherein the engagement module is further configured to evaluate relative motion between the health monitor and the user based at least in part on data output by the supplemental engagement sensor.

* * * * *